United States Patent [19]

Laugier et al.

[11] Patent Number: 5,262,150
[45] Date of Patent: Nov. 16, 1993

[54] ANTIFUNGUS COMPOSITION IN DRY SPRAY FORM

[75] Inventors: Jean-Pierre Laugier, Antony; Francois Ringenbach, Bagneu; Philippe Touzan, Vanves, all of France

[73] Assignee: L'Oreal, Paris, France

[21] Appl. No.: 766,356

[22] Filed: Sep. 26, 1991

[30] Foreign Application Priority Data

Sep. 26, 1990 [FR] France .................. 90 11886

[51] Int. Cl.⁵ .............. A01N 25/06; A01N 33/04
[52] U.S. Cl. ........................ 424/47; 424/409; 424/489; 424/46; 514/741
[58] Field of Search .......... 424/405, 84, DIG. 10, 424/46, 404, 78.06, 47

[56] References Cited

U.S. PATENT DOCUMENTS 4,806,338  2/1989  Smith ........................ 424/47
4,882,359  11/1989  Nakagawa et al. .......... 514/947

FOREIGN PATENT DOCUMENTS 298271  1/1989  European Pat. Off. .
343843  11/1989  European Pat. Off. .
113920  6/1971  France .
229753  12/1974  France .

OTHER PUBLICATIONS

The Merck Index, 11th Edition, 1989, p. 1442, Merck & Co., Rahway, US, No. 9086: "Terbinafine".

*Primary Examiner*—Thurman K. Page
*Assistant Examiner*—Neil Levy
*Attorney, Agent, or Firm*—Cushman, Darby & Cushman

[57] ABSTRACT

An antifungus composition in dry spray form contains in combination at least one antifungus agent of the family of allylamines, a noncyclized silicone polymer, a mineral or organic charge and a gas propellant. This composition is useful in the treatment of mycoses.

8 Claims, No Drawings

ANTIFUNGUS COMPOSITION IN DRY SPRAY FORM

The present invention relates to a new dermatologic composition in the form of a spray for the pharmaceutical treatment of mycoses. This composition contains an antifungus agent in combination with a noncyclized silicone polymer.

Compositions in the form of a dry spray are known in the pharmaceutical field and are, in particular, employed for the treatment of oozing mycoses. In effect, the powder form is quite adapted to this type of cutaneous disorder and its use with the aid of an aerosol is routine.

For example, there exist on the market dry powder sprays based on econazole nitrate or tolnaphthate.

However, for this type of spray there are some disadvantages which are connected with concentration of the active principle which can be re-established after spraying with regard to the concentration of this same active principle inside the aerosol container. Moreover, the sprayings do not re-establish the same amount of the active principle over the course of time.

Therefore it is a purpose of the present invention to insure that the concentration of the active principle in the powdered spray, after spraying, is identical or near to it in the powder contained in the aerosol container, that is to say that the spray must re-establish after spraying, the same percentage of active principle as that contained in the powder in the container.

It is appropriate, moreover, to insure that each successive spraying re-establishes the same or nearly the same amount of active principle, which means that the spraying must be perfectly homogeneous over the course of time.

Until now, the solution to these problems consisted in overdosing the powder with the active principle before packaging in order to obtain, at the nozzle outlet, the desired concentration. This practice, however, involved an obvious increase in production costs.

Moreover, it is often necessary, in order to avoid technical clogging problems, for example, at the nozzle, to micronize the powder before packaging it into an aerosol container. This also represents a costly operation, or indeed increases the pressure of the gas propellant in the aerosol container, which in turn causes, during use, a significant cooling of the skin.

It has now been noted in a quite unexpected manner that the addition of certain silicone polymers to the powder contained in the dry spray provides a regular dosage of the antifungus active principle and also provides essentially an identical amount of this active principle in the powder containing in the aerosol container and in the powder delivered after spraying.

Until now, the combination of silicone polymers with pharmaceutical dry sprays has not been described, although in the cosmetic field their use in antiperspirant aerosols has been described, for example, in U.S. Pat. No. 4,806,338. However, this patent is concerned with antiperspirant compositions whose active compounds are very often hygroscopic compounds. In this type of composition, silicone polymers play the role of an antihygroscopic agent by protecting solid particles rapidly absorbing moisture and by improving the skin adherence qualities of the powder after spraying.

Among other aerosol cosmetic compositions which contain silicones, mention can be made of "wet" sprays, that is, those that also contain an organic solvent. In these products, the silicone plays several roles, such as, for example, the role of a solvent (British patent No. 1.167.173 and French patent No. 2.113.920) or even the role of retarding solvent evaporation thereby improving the quality of the droplets of the "wet" spray (U.S. Pat. No. 4,152,416 and European patent No. 343,843).

The present invention, on the other hand, relates to a dry spray pharmaceutical composition containing an antifungus agent of the family of allylgmines. Preferably this antifungus agent is terbinafin or naftifin or their salts and principally their hydrochlorides.

Terbinafin is sold by Sandoz under the name "LAMISIL" (trade name) and is described in European patent No. 024,587.

It possesses antifungus properties in the measure where it inhibits the biosynthesis of sterols of membranes by intervening with respect to epoxidase squalene enzyme thus preventing the synthesis of ergosterol which is indispensable to fungus.

This characteristic renders terbinafin very effective with respect to dermatophytes such as, for example, *Trichophyton rubrum, Epidermophyton floccusum, Trichophyton mentagrophytes, microsporum camis* and *Trichophyton tonsurans.*

Moreover, terbinafin, as well as naftifin also intervenes with respect to the metabolism of RNAN by inhibiting the RNA-polymerase and it also intervenes with respect to synthesis of membranes by inhibiting the chitin synthetase of *Saccharomyces cerevisiae.*

This activity explains the effectiveness of terbinafin on various species of Aspergillus, Candida and Fusarium.

The antifungus agents of the family of allylamines have principally no hygroscopic character.

The present invention thus relates to an antifungus composition in the form of a dry spray characterized by the fact that it contains, in combination, at least one antifungus agent of the family of allylamines, at least one noncyclized silicone polymer, at least one mineral or organic charge or filler and at least one propellant.

In a general manner, the antifungus composition according to the invention can contain by weight relative to the total weight of the composition:

from 0.01 to 0.25 percent and preferably from 0.04 to 0.15 percent of the antifungus agent, from 0.01 to 1.25 percent and preferably from 0.04 to 0.6 percent of noncyclized silicone polymer, from 0.01 to 40 percent and preferably from 0.1 to 20 percent of mineral or organic charge, and from 85 to 95 percent of the propellant.

In effect, based on some studies, it has been noted that the noncyclized silicone polymers contribute, in the case of the allylamines, a solution to the problem of equivalent dosage between the powder in the aerosol container and the powder leaving the aerosol container, without it being necessary to overdose the active principle in the powder packaged in the aerosol container.

On the other hand, the noncyclized silicon polymers progressively maintain the strength of the active principle during the use of the spray.

Representative noncyclized silicone polymers usefully employed in accordance with the present invention include dimethicones (DM) having the general structure:

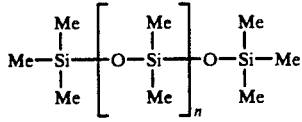

wherein n ranges from 3 to 2,000 and preferably from 20 to 1,000. Such products are sold under the trade name "BELSIL DM 0, 65, 35, 100 AND 350" by Wacker;

phenyldimethicones (PDM) having the general structure:

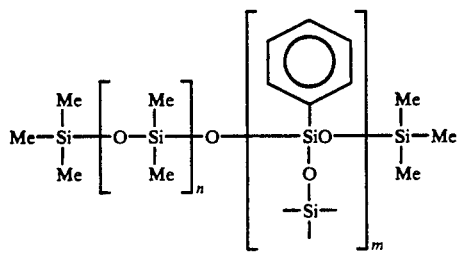

wherein n and m range from 5 to 2,000 and preferably from 20 to 1000. Such products are sold under the trade name "BELSIL PDM 20, 200 and 1000" by Wacker;

phenyltrimethicones (PTM) having the general structure:

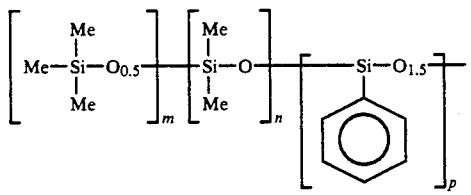

wherein m, n and p, each independently, range from 2 to 2,000 and preferably from 20 to 1,000. Such products are sold by Goldschmidt under the trade names "ABIL AV 20, 200 and 2000";

dimethicone copolyols (DMC) having the general structure

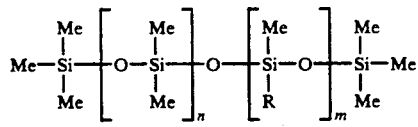

wherein n and m range from 2 to 2,000 and preferably between 20 and 1,000, R is a straight or branched copolyol chain having the formula:

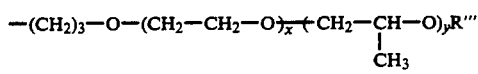

wherein x and y range from 1 to 20 and

R''' is a straight or branched chain alkyl having 10 to 18 carbon atoms. Such products are sold under the trade names "BELSIL DMC 6031, 6032, 6033 and 6035" by Wacker;

stearoxydimethicones (SDM) having the general structure:

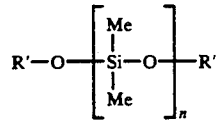

wherein

R' is a straight or branched chain alkyl having 3 to 20 carbon atoms and n ranges from 3 to 2,000.

Such products are sold under the trade names "BELSIL SDM 6021 and 6022" by Wacker; and aminofunctional silicones (SAM) having the general structure:

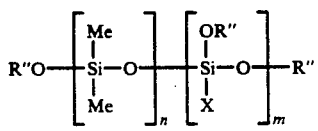

wherein n and m range from 2 to 2,000 and preferably from 20 to 1,000, each R" represents, independently, H, $CH_3$ or $Si(CH_3)_3$ and X represents $-(CH_2)_3-NHCH_2CH_2NH_2$.

Representative aminofunctional silicones include the product sold under the trade name "AMODIMETHICONE" by Wacker.

Preferably employed are non-volatile silicone polymers in oil form having a viscosity between 5 and 15,000 centistokes (5 and $15,000 \times 10^{-6}$ m²/s). However, viscosity does not constitute a critical property in order to secure good implementation of the present invention.

The silicone polymers are employed in an amount of 0.1 to 10 weight percent, preferably 0.5 to 5 weight percent based on the weight of the powder phase.

The antifungus agent is present in an amount ranging from 0.1 to 2 weight percent and preferably 0.5 to 1.5 weight percent based on the weight of the powder phase.

The propellants can be liquefiable aliphatic hydrocarbons such as propane, butane, isobutane, pentane, isopentane, neopentane and mixtures thereof. Halogenated hydrocarbons can also be employed and they include chlorofluoroalkanes such as monochlorodifluoromethane, monochlorodifluoroethane and mixtures thereof.

The powder phase/propellant weight ratio ranges between 1-8 and 1-12.

Representative mineral or organic charges include colloidal silica, zinc oxide, talc, microcrystalline tristearate and zinc stearate.

Preferably, anhydrous colloidal silica is employed as the mineral charge, optionally in combination with at least one other mineral or organic charge. Colloidal silica principally facilitates suspending the powder in the liquid propellant before each use. It can be employed at a rate of 0.1 to 5 weight percent, preferably 1 to 2 weight percent, relative to the weight of the powder phase or from 0.01 to 0.6 weight percent and preferably from 0.1 to 0.25 weight percent relative to the total weight of the composition.

Finally, perfumes and/or preservatives such as benzyl alcohol can be introduced into the compositions of the present invention.

The composition in the form of a powder spray according to the invention is particularly indicated for treating difficultly accessible areas on the one hand and macerated mycoses on the other hand such as

| genital intertrigo | } due to various |
| under the breast intertrigo | species of Candida |
| marginal Hebra eczema | } due to various species |
| athlete's foot | of dermatophytes |
| tinea | |

Regular use of the powder spray form composition according to the invention, when it contains 0.1 percent of an antifungus agent, such as terbinafin, can provide complete healing of the lesions when employed at a rate of 2 applications per day.

The following nonlimiting examples illustrate the present invention.

EXAMPLE 1

Dry Spray with 0.1% of terbinafin hydrochloride

| | |
|---|---|
| Micronized talc | 8.5 g |
| Colloidal silica | 0.1 g |
| Microcrystalline glycerol tristearate | 0.8 g |
| Dimethicone - "BELSIL DM 100" sold by Wacker | 0.5 g |
| Terbinafin hydrochloride | 0.1 g |
| Propellant: 40/60 mixture of dichloro-tetrafluoroethane/dichloro-difluoromethane, sufficient amount for | 100 g |

There are introduced into a conventional powder mixer, terbinafin hydrochloride, micronized talc, glycerol tristearate and then the silica. After mixing until the product is homogeneous, the silicone polymer is progressively added. After stirring, a powder is obtained which no longer adheres to the walls of the mixer. The powder is then introduced into an aerosol container which is sealed. The propellant mixture is then introduced into the container.

In the same manner as that for Example 1 the compositions of Examples 2 and 3 are prepared.

EXAMPLE 2

Dry Spray with 0.1% of terbinafin hydrochloride

| | |
|---|---|
| Zinc oxide | 4.0 g |
| Colloidal silica | 0.2 g |
| Talc | 4.7 g |
| Phenyldimethicone - "BELSIL PDM 200", sold by Wacker | 1.0 g |
| Terbinafin hydrochloride | 0.1 g |
| Propellant - butane, sufficient amount for | 100 g |

EXAMPLE 3

Dry Spray with 0.1% naftifin hydrochloride

| | |
|---|---|
| Zinc oxide | 4.3 g |
| Colloidal silica | 0.1 g |
| Talc | 5.0 g |
| Stearoxydimethicone - "BELSIL SDM 6021", sold by Wacker | 0.6 g |
| Naftifin hydrochloride | 0.1 g |
| Propellant: 40/60 mixture of dichloro-tetrafluoroethane/dichloro-difluoromethane, sufficient amount for | 100 g |

EXAMPLE 4

Dry Spray with 0.1% of terbinafin hydrochloride

| | |
|---|---|
| Zinc oxide | 4.1 g |
| Talc | 4.2 g |
| Colloidal silica | 0.2 g |
| Dimethicone-copolyol - "BELSIL DMC 6031", sold by Wacker | 0.8 g |
| Terbinafin hydrochloride | 0.1 g |
| Benzyl alcohol | 0.3 g |
| Propellant: butane, sufficient amount for | 100 g |

To prepare this spray, the following operation is carried out.

Into a mixer equipped with a powder cutter, there are introduced zinc oxide, talc and colloidal silica. After mixing, the terbinafin hydrochloride in solution in benzyl alcohol is added to the preparation. Mixing is again carried out until a homogeneous product is obtained. At the time of packaging, the silicone polymer is directly introduced into the aerosol container, followed by introducing the powder phase containing terbinafin hydrochloride. The aerosol containers are then sealed and pressurized by the addition of the propellant.

EXAMPLE 5

Dry spray with 0.1% of naftifin hydrochloride

| | |
|---|---|
| Micronized talc | 5.9 g |
| Zinc stearate | 3.1 g |
| Colloidal silica | 0.5 g |
| Naftifin hydrochloride | 0.1 g |
| "Amodimethicone" sold by Wacker | 0.4 g |
| Propellant: butane, sufficient amount for | 100 g |

EXAMPLE 6

Dry spray with 0.1% terbinafin hydrochloride

| | |
|---|---|
| Micronized talc | 9.0 g |
| Colloidal silica | 0.4 g |
| Phenyltrimethicone, sold under the trade name "ABIL AV 20" by Goldschmidt | 0.5 g |
| Terbinafin hydrochloride | 0.1 g |
| Propellant: isobutane, sufficient amount for | 100.0 g |

We claim:

1. An antifungus composition in the form of a dry powder spray packaged in an aerosol container, said composition comprising in combination at least one antifungus agent selected from terfibafin, naftifin and salts thereof, at least one noncyclized silicone polymer selected from a dimethicone, a phenyldimethicone, a phenyltrimethicone, a dimethicone-copolyol, a stearoxydimethicone and an aminofunctional silicone in an amount effective to insure that the concentration of said antifungus agent in the powdered spray, after spraying, is identical or nearly identical to the concentration in the powder contained in the aerosol container, at least one mineral or organic charge and at least one propellant and wherein said composition contains by weight relative to the total weight of said composition from 0.01 to 0.25 percent of said antifungus agent, from 0.01 to 1.25 percent of said noncyclized silicone polymer, from 0.01 to 40 percent of said mineral or organic charge, and from 85 to 95 percent of said propellant.

2. The antifungus composition of claim 1 containing by weight relative to the total weight of said composition from 0.04 to 0.15 percent of said antifungus agent,
from 0.04 to 0.6 percent of said noncyclized silicone polymer,
from 0.1 to 20 percent of said mineral or organic charge, and
from 85 to 95 percent of said propellant.

3. The antifungus composition of claim 1 wherein said mineral or organic charge is selected from colloidal silica, zinc oxide talc, a microcrystalline tristearate and zinc stearate.

4. The antifungus composition of claim 1 wherein said mineral charge is colloidal silica present in an amount ranging from 0.1 to 0.6 percent by weight.

5. The antifungus composition of claim 1 wherein said mineral charge is colloidal silica present in an amount ranging from 0.1 to 0.25 percent by weight.

6. The antifungus composition of claim 1 wherein said propellant is selected from a liquefiable aliphatic hydrocarbon and a halogenated hydrocarbon.

7. The antifungus composition of claim 6 wherein said liquefiable aliphatic hydrocarbon is selected from propane, butane, isobutane, pentane, isopentane and neopentane.

8. The antifungus composition of claim 6 wherein said halogenated hydrocarbon is selected from monochlorodifluoroethane, monochlorodifluoromethane and mixture thereof.

* * * * *